(12) United States Patent
Miocinovic et al.

(10) Patent No.: US 11,712,564 B2
(45) Date of Patent: Aug. 1, 2023

(54) SYSTEMS AND METHODS FOR AUTOMATED DEEP BRAIN STIMULATION PROGRAMMING

(71) Applicant: Emory University, Atlanta, GA (US)

(72) Inventors: Svjetlana Miocinovic, Atlanta, GA (US); Babak Mahmoudi, Atlanta, GA (US); Parisa Sarikhani, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/315,129

(22) Filed: May 7, 2021

(65) Prior Publication Data

US 2021/0346699 A1 Nov. 11, 2021

Related U.S. Application Data

(60) Provisional application No. 63/022,166, filed on May 8, 2020.

(51) Int. Cl.
*A61N 1/36* (2006.01)
*A61N 1/05* (2006.01)
(52) U.S. Cl.
CPC ....... *A61N 1/36067* (2013.01); *A61N 1/0534* (2013.01); *A61N 1/36175* (2013.01); *A61N 1/36178* (2013.01); *A61N 1/36192* (2013.01)
(58) Field of Classification Search
CPC ............. A61N 1/36067; A61N 1/0534; A61N 1/36175; A61N 1/36178; A61N 1/36192;
(Continued)

(56) References Cited

U.S. PATENT DOCUMENTS 7,184,837 B2   2/2007  Goetz
8,684,921 B2   4/2014  Osorio
(Continued)

OTHER PUBLICATIONS

3. Moran et al., "Real-Time Refinement of Subthalamic Nucleus Targeting Using Bayesian Decision-Making on the Root Mean Square Measure", Movement Disorders, 21: 1425-1431. published online Jun. (Year: 2006).*

(Continued)

*Primary Examiner* — Carl H Layno
*Assistant Examiner* — Anh-Khoa N Dinh
(74) *Attorney, Agent, or Firm* — Emory Patent Group

(57) ABSTRACT

The systems and methods can automatically determine a patient-specific set of stimulation parameters using optimization for exploring and/or programming a neurostimulation device, e.g., deep brain stimulation (DBS). In one implementation, the method may include receiving patient data and set of stimulation parameters associated stimulation delivered to a patient by a neurostimulation device. The method may include determining one or more objective metrics using the patient data for each set of stimulation parameters. The one or more objective metrics may be a quantitative value that represents a rating or score of tremor severity and/or side effect severity. The method may further include generating a patient specific response model using the one or more objective metrics and the associated set of stimulation parameters. The method may also include applying an optimization algorithm to the generated response model to determine a candidate set of one or more stimulation parameters.

20 Claims, 8 Drawing Sheets

(58) Field of Classification Search
CPC ............ A61N 1/36139; A61N 1/36146; A61N 1/36185; A61N 1/37247; A61N 1/3605; A61N 1/372; A61N 1/0551; A61N 1/0556; A61N 1/36003; A61N 1/36132; A61N 1/36135; G16H 50/30; G16H 50/50

See application file for complete search history.

(56) References Cited

U.S. PATENT DOCUMENTS

| | | | |
|---|---|---|---|
| 8,774,923 | B2 | 7/2014 | Rom |
| 9,037,256 | B2 | 5/2015 | Bokil |
| 9,119,964 | B2 | 9/2015 | Marnfeldt |
| 9,561,380 | B2 | 2/2017 | Carcieri et al. |
| 9,662,502 | B2 | 5/2017 | Giuffrida et al. |
| 9,707,404 | B2 | 7/2017 | Rao et al. |
| 9,792,412 | B2 | 10/2017 | Moffitt et al. |
| 9,802,052 | B2 | 10/2017 | Marnfeldt |
| 9,943,689 | B2 | 4/2018 | Cecchi et al. |
| 10,195,439 | B2 | 2/2019 | Steinke et al. |
| 10,842,997 | B2 | 11/2020 | Moffitt et al. |
| 2009/0118786 | A1 | 5/2009 | Meadows et al. |
| 2010/0137734 | A1* | 6/2010 | Digiovanna ............ A61F 2/72 600/545 |
| 2017/0197086 | A1 | 7/2017 | Howard et al. |
| 2018/0028826 | A1* | 2/2018 | Carcieri ............ A61N 1/36185 |
| 2018/0078770 | A1 | 3/2018 | Rickert et al. |

OTHER PUBLICATIONS

Grahn et al. "A neurochemical closed-loop controller for deep brain stimulation: toward individualized smart neuromodulation therapies." Frontiers in Neuroscience, 2014; 8:169.

Teplitzky et al. "Model-Based Comparison of Deep Brain Stimulation Array Functionality with Varying Number of Radial Electrodes and Machine Learning Feature Sets." Frontiers in Computational Neuroscience, 2016;10:58.

Su et al. "Nonlinear predictive control for adaptive adjustments of deep brain stimulation parameters in basal ganglia-thalamic network." Neural Networks, 2018;98:283-295.

* cited by examiner

SYSTEMS AND METHODS FOR AUTOMATED DEEP BRAIN STIMULATION PROGRAMMING

CROSS-REFERENCE TO RELATED APPLICATIONS

This application claims the benefit of U.S. Provisional Application No. 63/022,166 filed May 8, 2020. The entirety of this application is hereby incorporated by reference for all purposes.

STATEMENT REGARDING FEDERALLY SPONSORED RESEARCH OR DEVELOPMENT

This invention was made with government support under NS098685 awarded by the National Institutes of Health. The government has certain rights in the invention.

BACKGROUND

Deep Brain Stimulation (DBS) systems has become a standard treatment for neurological disorders such as Parkinson's disease (PD) and essential tremor (ET), to ameliorate patients' motor symptoms when medications are insufficient. Selection of stimulation parameters (electrode contact and configuration, amplitude, pulse width and frequency) are generally patient-specific due to each person's unique anatomy, symptomatology and DB S electrode location.

Currently, these systems are manually programmed. Manual programming of these systems can be a time-consuming process requiring specially trained clinicians to work with each patient over several months and multiple visits in a specialized center to achieve appropriate results, as well as can require each patient undergo numerous clinical tests during each visit. Currently available automatic methods generally rely on a brute-force method that can require patients to undergo the same number of tests as manual programming even if the optimal parameter setting is already achieved. Prolonged programming sessions could exhaust the patients thereby affecting the quality and accuracy of these tremor evaluation tests.

SUMMARY

Thus, there is a need for automated and efficient determination of an optimal set of stimulation parameters.

Techniques disclosed herein relate generally to automatically determining a patient-specific set of stimulation parameters using optimization for exploring and/or programming a neurostimulation device, such as a deep brain stimulation (DBS) device. The set of stimulation parameters can be determined by using a patient-specific response model generated from objective metrics and associated stimulation parameters collected during a period of time, such as during one or more testing sessions. The techniques can automatically determine an optimal set of stimulation parameters using a limited number of data points and therefore can efficiently and accurately program a neurostimulation device.

The disclosed embodiments may include computer-implemented systems and methods for determining an optimal set of stimulation parameters for a neurostimulation device. In some embodiments, a method may include receiving patient data and set of stimulation parameters associated stimulation delivered by a neurostimulation device to a patient for a period of time. The method may further include determining one or more objective metrics using the patient data for each set of stimulation parameters for the period of time. The one or more objective metrics may be a quantitative value that represents (i) a rating or score of tremor severity and/or (ii) a rating or score of side effect severity associated with the set of stimulation parameters. The method may further include generating a response model specific to the patient using the one or more objective metrics and the associated set of stimulation parameters. The method may also include applying an optimization algorithm to the generated response model to determine a candidate set of one or more stimulation parameters.

In some embodiments, the system may include one or more processors; and one or more hardware storage devices having stored thereon computer-executable instructions. The instructions may be executable by the one or more processors to cause the computing system to perform at least receiving patient data and set of stimulation parameters associated stimulation delivered by a neurostimulation device to a patient for a period of time. The one or more processors may be further configured to cause the computing system to perform at least determining one or more objective metrics using the patient data for each set of stimulation parameters for the period of time. The one or more objective metrics may be a quantitative value that represents (i) a rating or score of tremor severity and/or (ii) a rating or score of side effect severity associated with the set of stimulation parameters. The one or more processors may also be configured to cause the computing system to perform at least generating a response model specific to the patient using the one or more objective metrics and the associated set of stimulation parameters. The one or more processors may be further configured to cause the computing system to perform at least applying an optimization algorithm to the generated response model to determine a candidate set of one or more stimulation parameters.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, the emphasis being placed upon illustrating the principles of the disclosure.

FIG. 4A demonstrates the modeled effect of stimulation settings on the clinical scores evaluated by neurologists. FIG. 4B shows the same model on predicted clinical scores modeled by a multinomial logistic regression method for the same patient.

FIG. 5A shows the results of GPR modeling for one patient for a rest test, FIG. 5B shows the results of GPR modeling for one patient for a kinetic tremor test, and FIG. 5C shows the results of GPR modeling for one patient for a postural tremor test.

FIG. 6A illustrates the trajectory of points that was selected by the acquisition function to be evaluated at each iteration during one trial of running the optimizer.

DESCRIPTION OF THE EMBODIMENTS

Figure 1:
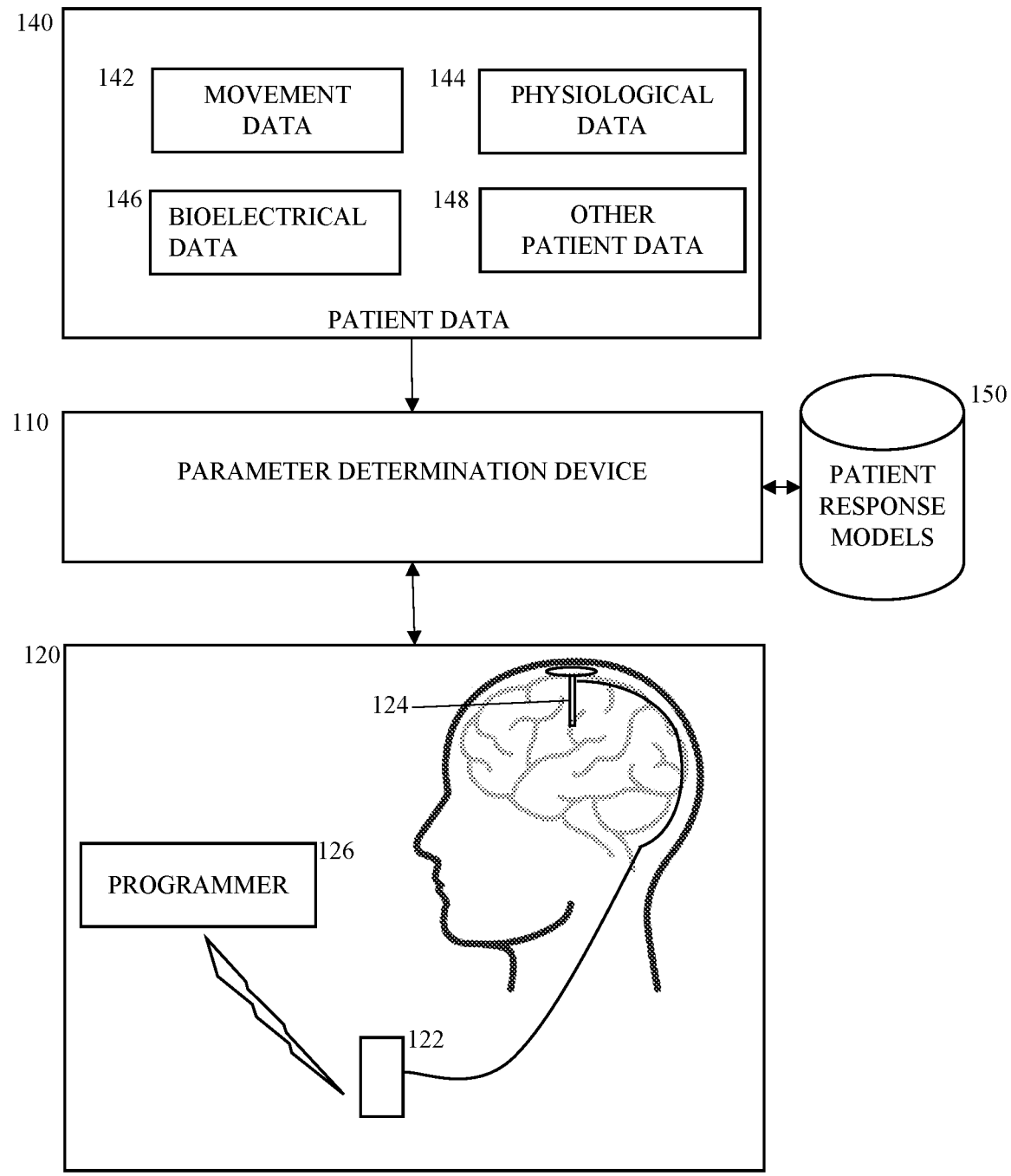
FIG. 1 illustrates an example of system environment for determining an optimal set of stimulation parameters according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosed embodiments relate to techniques for automatically determining a candidate set of stimulation parameters using machine learning techniques to explore and/or program a neurostimulation device, such as deep brain stimulation (DBS). Various embodiments are described herein, including systems, methods, devices, modules, models, algorithms, networks, structures, processes, computer-program products, and the like.

DBS programming is commonly performed by specialized clinicians, such as movement disorder neurologists, neurosurgeons, fellows, occupational and physical therapists, nurses, or employees of the DBS manufacturer at a specialized site. Many patients have inadequate access to DBS programming due to geographical location of the specialized site and/or specialized clinicians.

Programming approaches and experience can vary greatly across institutions. Generally, programming can rely on iterative approach whereby new parameters are determined during programming sessions based primarily on subjective clinician calculation and observation of results of tests and patient feedback. Often, many clinicians make educated guesses as to the best settings based on their prior experience and the programming sessions can require multiple iterations before reaching an optimal set of stimulation parameters. Prolonged programming sessions could exhaust the patients thereby affecting the quality and accuracy of the results of the tests, such as tremor evaluation tests. Thus, accuracy and efficiency can vary vastly across institutions. Additionally, programming session can be quite time consuming and costly.

The disclosure addresses these deficiencies. The disclosure relates to automatically and efficiently determining a candidate set of stimulation parameters that could be an optimal set of stimulation parameters using machine learning techniques to explore for a neurostimulation device, such as deep brain stimulation (DBS). The disclosure can determine a candidate set of stimulation parameters by optimizing patient specific response model(s) generated from patient-specific objective metrics of tremor severity and/or side effects. The patient specific response model can act as a surrogate model of the patient response to stimulation. So the disclosure optimize can approximate model of the patient response (surrogate model) using a limited number of data points (stimulation parameter/objective metric pairs) to ultimately determine an optimal set of stimulation parameters and does not require collecting lots of data. The disclosure can there more efficiently, quickly, and accurately determine an optimal set of stimulation parameters.

While the process of optimize the set of stimulation parameters may be iterative, the disclosure significantly minimizes, or at least greatly reduces the time and expertise required to arrive at optimized set of stimulation parameters, advantageously allowing clinicians, technicians or physicians with lesser training or experience to adjust parameter settings during patient visits, and to do so in less time than is currently required. Additionally, the disclosure can increase access to geographically disparate populations by putting the expertise into the system and reducing or eliminating the need for an expert or trained clinician to be present with each patient.

While examples of the disclosure may be specific to determining an optimal/candidate set of stimulation parameters for deep brain stimulation, it will be understood that these examples are nonlimiting and that the methods and systems may be used to determine a set of stimulation parameters for any other type of system, now known or later developed, that applies therapeutic neurostimulation to neurological systems. Additionally, the disclosure can be used for applications other than deep brain stimulation, including spinal cord stimulation, peripheral nerve stimulation, dorsal root ganglion stimulation, cortical stimulation, vagal nerve stimulation, as well as stimulation of other nerves, muscles, and tissues.

FIG. 1 depicts an example system environment 100 for determining an optimal set/a candidate set of stimulation parameters for exploring and/or programming a neurostimulation device according to embodiments. The set of stimulation parameters may relate to one or more stimulation settings for delivery of neurostimulation, such as electrode configuration, amplitude, pulse width, pulse rate, duration, among others, or a combination thereof. Electrode configurations can specify electrode combinations and polarities for an electrode set implanted in a patient. For example, electrode configurations may further define one or more settings such as amplitudes, pulse widths, pulse rates, and durations of stimulation energy delivered by specific electrodes in the electrode configuration.

A candidate set of stimulation parameters may be considered an "optimal" set of stimulation parameters if the candidate meets certain criteria. For example, the criteria may be designated or settable (variable) and refer to attributes such as: 1) termination state of the optimization (e.g., maximum number of iterations of candidate sets); 2) convergence to a solution (e.g., minimizes or maximizes an objective function); and/or 3) therapeutic outcome in which a patient exhibits optimal symptomatic benefits without side effects as defined by the objective metrics.

The system 100 may include a parameter determination device 110 that can be used to determine an optimal/candidate set of stimulation parameters for a neurostimulation system 120 for delivering deep brain stimulation to a patient. In some embodiments, the parameter determination device 110 may include any computing or data processing device consistent with the disclosed embodiments. In some embodiments, the parameter determination device 110 may incorporate the functionalities associated with a personal computer, a laptop computer, a tablet computer, a notebook computer, a hand-held computer, a personal digital assistant, a portable navigation device, a mobile phone, an embedded device, a smartphone, and/or any additional or alternate computing device/system. The parameter determination device 110 may transmit and receive data across a communication network.

In some embodiments, the neurostimulation system 120 may be an implantable electrical stimulation system that delivers neurostimulation therapy to a patient. The device may be a DBS system that provides electrical stimulation therapy directly to tissue within the brain of a patient, e.g., a tissue under the dura mater of the brain or one or more branches or nodes, or a confluence of fiber tracks. For example, the neurostimulation system 120 may be a brain pacemaker, which sends electrical impulses, through implanted electrodes, to specific parts of the brain (brain nucleus) for the treatment of movement and affective disorders. By way of example, to manage movement disorders, such as Parkinson's disease, the electrodes may be positioned to deliver stimulation to one or more regions of brain, such as the subthalamic nucleus, globus pallidus or thalamus.

The neurostimulation system 120 may be can be any currently available or later developed neurostimulation systems, such as those from several companies (e.g., Medtronic, Boston Scientific, Neuromed, Cochlear Corp., Advanced Bionics, etc.), that can deliver neurostimulation therapy to a patient in the form of electrical pulses or other neuromodulatory actions (e.g., such as optimal stimulation, magnetic stimulation, etc.). By way of example, the neurostimulation system 120 may include an implanted pulse generator (IPG) 122 that is electrically connected to one or more leads 124 implanted in a patient, for example, by one or more extensions (e.g., insulated wire). The patient may be a human, non-human primate (NHP), or another animal. Each lead can include one or more of stimulation electrodes configured to deliver electrical stimulation to a tissue site within the brain of the patient and/or one or more sensing electrodes configured to sense neurological brain signals within the brain of the patient.

For example, the IPG 122 can be a battery-powered neurostimulator. The IPG 122 can send electrical pulses via the stimulation electrodes of the lead(s) 124 placed in the brain to interfere with neural activity at the target site. For example, the IPG 122 may include pulse generation circuitry that delivers electrical stimulation energy in the form of, for example, a pulsed electrical waveform (i.e., a temporal series of electrical pulses) to the electrode(s) in accordance with a set of stimulation parameters. The IPG 122 can be implanted into a patient's body, for example, below the patient's clavicle area or within the patient's buttocks or abdominal cavity. The IPG 122 can have stimulation channels that may be independently programmable to control the magnitude of the current stimulus from each channel. The IPG 122 may include a hermetic housing to substantially enclose components, such as a processor, therapy module, and memory.

In some embodiments, the IPG 122 can include a memory to store a plurality of therapy programs that each define a set of stimulation parameters for therapy. In some examples, the IPG 122 may select a therapy program from the memory, for example, based on various parameters, such as patient sensing data. The IPG 122 may generate electrical stimulation based on the stimulation parameters of the selected program to manage the patient symptoms associated with a movement disorder. For example, where the IPG 122 delivers electrical stimulation in the form of electrical pulses, the set of stimulation parameters may include amplitude mode (constant current or constant voltage), pulse amplitude, pulse width, a waveform shape, among others, or any combination thereof. In addition, if different electrodes are available for delivery of stimulation, the set of stimulation parameters may be further characterized by an electrode combination, that may define selected electrodes and their respective polarities.

By way of further example, the neurostimulation system 120 can also include one or more of an external remote control (RC), a clinician's programmer (CP), and/or power source (e.g., an internal power source (e.g., rechargeable battery) and/or an external power source (e.g., charger)).

In some examples, the IPG 122 may include a sensing module that is configured to sense bioelectrical signals within one or more regions of brain via a subset of electrodes. Accordingly, in some examples, electrodes that may be used to deliver electrical stimulation to target sites within brain as well as sense brain signals within the brain. In some examples, the IPG 122 can also use a separate set of sensing electrodes to sense the bioelectrical brain signals.

In some examples, bioelectrical signal(s) of patient may be monitored with external electrodes, e.g., scalp electrodes. Moreover, in some examples, the sensing circuitry that senses bioelectrical signals of brain (e.g., the sensing circuitry that generates an electrical signal indicative of the activity within brain) can be in a physically separate housing from the IPG 122.

The bioelectrical signals sensed by the IPG 122 may reflect changes in electrical current produced by the sum of electrical potential differences across brain tissue. Example bioelectrical brain signals may include, but are not limited to, an electroencephalogram (EEG) signal, an electrocorticogram (ECoG) signal, a local field potential (LFP) sensed from within one or more regions of a patient's brain, a micro electrode recording (MER) and/or action potentials from single cells within the patient's brain. In some examples, LFP data can be measured ipsilaterally or contralaterally and considered as an average (e.g., a maximum or minimum or a heuristic combination thereof) or as some other value. The location at which the sensed signals are obtained may be adjusted according to a disease onset side of the body of a patient or severity of symptoms or disease duration. The adjustments, may, for example, can be made on the basis of clinical symptoms presented and their severity, which can be augmented or annotated with recorded LFP data.

In some examples, the IPG 122 may be configured to deliver electrical stimulation therapy to brain of patient in an open loop manner, in which the IPG 122 delivers the stimulation therapy according to the set of programmed parameters without intervention from a user or a sensor. In other examples, the IPG may be configured to deliver electrical stimulation therapy to the brain of the patient in a closed loop manner, in which the IPG 122 controls the timing of the delivery of electrical stimulation to brain, the output parameters of the electrical stimulation, or both based on the set of programmed parameters and input from one or more sensing sources.

The system 120 may include an external device 126 configured to wirelessly communicate with IPG 122, for example, to provide using radio frequency (RF) telemetry techniques known in the art, as needed to provide therapy information (e.g., set of stimulation parameters) or retrieve therapy information (e.g., bioelectrical brain signals). The device 126 may be an external computing device that the user, e.g., the clinician and/or patient, may use to communicate with the IPG 122. For example, the device 126 may be a clinician programmer that the clinician uses to communicate with the IPG 122 and program the one or more set of stimulation parameters for one or more therapy programs for the IPG 122. In addition, or instead, the device 126 may be a patient programmer that allows the patient to select programs and/or view and modify the parameter(s). The clinician programmer may include more programming features than the patient programmer. In other words, more complex or sensitive tasks may only be allowed by the clinician programmer to prevent an untrained patient from making undesired changes to the IPG 122.

The external device 126 may be a hand-held computing device, a larger workstation, separate application within another multi-function computing device (rather than a dedicated computing device), among others, or a combination thereof.

In some embodiments, the parameter determination device 110 may be configured to communicate with the IPG 122, the device 126, another programming or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. The device 126 may also communicate with other programming or computing devices, such as the device 110, via exchange of removable media, such as memory cards. In other embodiments, the device 126 and/or IPG 122 may incorporate the functionalities discussed and associated with the stimulation parameter device 110.

In some embodiments, the stimulation parameter device 110 may determine a candidate/optimal set of stimulation parameters for the system 120 by optimizing one or more patient-specific response models generated from objective metrics determined from (i) patient data 140 collected for a period of time, for example, during one or more testing sessions in which one or more tests are administered by a clinician and/or by the patient (e.g., at home) and (ii) the corresponding stimulation parameters associated with that period of time, such as each test. The patient data 140 may relate to passive and/or active behavioral and/or physiological and/or neurophysiological responses to various deep brain stimulation delivered by the device 120 according to a set of stimulation parameters.

In some embodiments, the patient data 140 may be acquired from one or more sources, such as external sensors, wearable device(s) having sensor(s), the device 120, the patient, or a combination thereof. In some embodiments, the patient data 140 may include movement data 142, physiological data 144, bioelectrical brain data 146, other patient data 148, among others, or any combination thereof.

By way of example, the movement data 142 may relate to a movement or acceleration of body part(s) measured by one or more sensors, for example, provided on a wearable device. For example, the one or more sensors may include but are not limited to accelerometer, gyroscope, magnetometer, among others, or a combination thereof. By way of example, the movement data 142 may be acquired using a wearable device during standard motor assessment tests that can be used to detect behavior responses, such as tremor or bradykinesia severity.

For example, the physiological data may include but is not limited to cardiac data, other physiological data that may relate to side effects induced by stimulation, among others, or any combination thereof. For example, the cardiac data may include Electromyography (EKG) measured by EKG sensor, electrocardiography (ECG) measured by ECG sensor, among others, or any combination thereof.

In some embodiments, the bioelectrical data 146 may include but is not limited to the bioelectrical data collected by the device 120 (e.g., LFP and ECoG), EEG detected by a non-invasive scalp sensor, among others, or any combination thereof.

The other patient data 148 may include but is not limited to results of patient self-assessments, questionnaires, results of memory tests (e.g., working task), and the like. For example, the patient self-assessment may be related to DBS-related side effects. In the self-assessment, a patient can report by rating or scoring DBS-related side effect severity associated with a delivery of a set of stimulation parameters. For example, the rating of severity or scoring can relate to the following levels of severity: no side effect, mild, moderate, and severe. Additionally, the rating/scoring of each report of a side-effect may include additional information, such as the type of side effect and affected areas.

The device 110 may determine one or more objective metrics of tremor suppression and/or side effect magnitude using the patient data 140, for example, collected during a testing session in which a plurality of different tremor assessment tests (e.g., rest, postural and kinetic) are administered using different stimulation parameters, during a period of time for which stimulation is delivered according to a set of stimulation parameters, among others, or any combination thereof. For example, each objective metric may be a quantitative value that reflects the efficacy of the corresponding stimulus parameter(s) used by the device 110 in terms of (i) a rating or score of tremor severity and/or (ii) a rating or score of side effect severity. The smaller the value of the objective value, the better is the efficacy of the corresponding DBS parameter(s).

In some examples, the movement data 142 and/or the bioelectrical data 146, can be used to determine the one or more objective metrics related to tremor suppression associated with a DBS parameter(s). By way of example, the one or more objective metrics may be a quantitative value representing a tremor severity rating or score associated with a stimulation delivered according by the device according to a set of stimulation parameters, for example, during a period of time, such as during one or more tests administered during a testing session.

For example, the movement data 142 collected from the inertial measurement sensors can be classified to determine tremor severity scores, for example, clinical tremor severity scores using a trained model based on a neurologist provided clinical rating according to the corresponding subitem on the Movement Disorders Society Unified Parkinson's Disease Rating Scale Part III (MDS-UPDRS III) subitems 3.15-3.17, using a trained model. By way of example, to train this predictive model, relevant time and frequency domain features, e.g. root mean square of the accelerometer and gyroscope data and tremor band power, can be calculated for a plurality of patients and fed along with the corresponding DBS parameter(s) into a classifier to predict for the clinical tremor rating for each set of DBS parameters.

For example, the score values predicted from the model can be numerical values ranging from 0-4 representing the level of patients tremor severity based on MDS-UPDRS III guidelines. The MDS-UPDRS III provides the following numerical ratings based on visual assessment: 0 for no tremor; 1 for slight tremor with amplitude less than 1 cm; 2 for mild tremor with amplitude between 1 cm and 3 cm; 3 for moderate tremor with amplitude between 3 cm and 10 cm; and 4 for severe tremor with amplitude greater than 10 cm.

For example, for the bioelectrical data 146, one or more of the objective metric(s) of tremor severity can be determined from EEG, ECoG, and/or LFP data. By way of example, the objective metric(s) may correspond to beta-band power, cortico-cortical coherence, and/or phase-amplitude coupling determined from the EEG, ECoG, and/or LFP data. For instance, with regards to Parkinsonian patients, the presence of rest tremor in Parkinsonian patients has been associated with reduced beta-band power in the cortex and subthalamic nucleus (STN), while presence of bradykinesia is associated with increased beta-band power; and rest tremor severity has been associated cortico-cortical coherence and/or phase-amplitude coupling.

In some examples, the patient self-assessment data can be used to determine the one or more objective metrics related to side effect severity. A quantitative score can be assigned to each side effect report. In the case of clinician-in-the-loop, the expert movement disorder neurologist could assign the scores based on patients' reports.

In some embodiments, the device 110 may generate one or more patient-specific response models using the one or more objective metrics and associated stimulation parameter(s). In some embodiments, a patient response model representing all of the objective metrics may be generated. For example, the one or more patient response models may be based on a single objective metric that is a combination of the determined objective metrics for tremor rating and side effect rating. This single objective metric may reflect the efficacy of each DBS parameter in terms of both tremor suppression and side effect magnitude. The smaller the objective value, the better is the efficacy of the corresponding DBS parameter. This way, the objective metric can reflect all targeted behavioral and/or neurophysiological measures as well as DBS-related side effects associated with each DBS parameter tested. By way of example, the single objective metric can be determined using an objective function.

In some embodiments, the device 110 may generate a multi-dimensional patient response model, where each dimension reflects one target objective metric, such as, tremor rating and side effect rating associated with the stimulation parameters used for different tremor assessment tests (rest, postural, kinetic). This scenario can be considered as multi-objective optimization where each dimension may represent a different objective measure or it might be considered as high-dimensional optimization task where the objective function is multi-dimensional. For example, parametric and/or nonparametric data-driven modeling techniques can be used to adaptively model a patient's response to DBS parameters as the automated system or the clinician interacts with the patient. Some examples of parametric models can include but are not limited to linear models and generalized linear models. An example of a non-parametric model can include Gaussian Process Regression (GPR) model. In some embodiments, artificial neural networks can be used.

The generated patient response model can be considered an approximate model of the patient response (surrogate model) using a limited number of data points (stimulation parameters/objective measures).

In some embodiments, the device 110 may determine a candidate set of stimulation parameters by applying a sequential model-based optimization algorithm to the one or more patient response models generated for a patient. In some examples, the sequential model-based optimization algorithm may rely on different probabilistic models such as Bayesian network structures to represent the patient's response to stimulation. In this case, the optimizer can sequentially build a surrogate model (patient response model) and evaluate the surrogate model. In single objective optimization tasks, there can be one response model. In multi-objective optimization tasks mixture surrogate models might be used. For example, the device 110 may use an acquisition function to determine a candidate set of stimulation parameters to test on the patient. The device 110 may then determine the one or more objective outcomes using the patient data 140 and the associated DBS parameters for that test and update the patient response model. The device 110 can determine that an candidate set of stimulation parameters is an optimal set, for example, after several iterations, when the candidate set meets the optimal criteria, such as convergence criteria.

In some embodiments, the device 110 may store the generated patient response models in a database 150 for future programming of the neurostimulation system 120 for each patient.

By employing an optimization algorithm that learns an optimal DBS settings, fewer number of tests on patients can be performed (vs. manual programming and/or brute-force programming method). Additionally, the optimization performed by the disclosure can improve sample efficiency and can be robust to measurement noise and variations of patient's response. This can result in better quality and accurate set of stimulation settings in quicker time.

Although the systems/devices of the environment 100 are shown as being directly connected, the device 110 may be indirectly connected to one or more of the other systems/devices of the environment 100. In some embodiments, the device 110 may be only directly connected to one or more of the other systems/devices of the environment 100.

It is also to be understood that the environment 100 may omit any of the devices illustrated and/or may include additional systems and/or devices not shown. It is also to be understood that more than one device and/or system may be part of the environment 100 although one of each device and/or system is illustrated in the environment 100. It is further to be understood that each of the plurality of devices and/or systems may be different or may be the same. For example, one or more of the devices of the devices may be hosted at any of the other devices.

Figure 2:
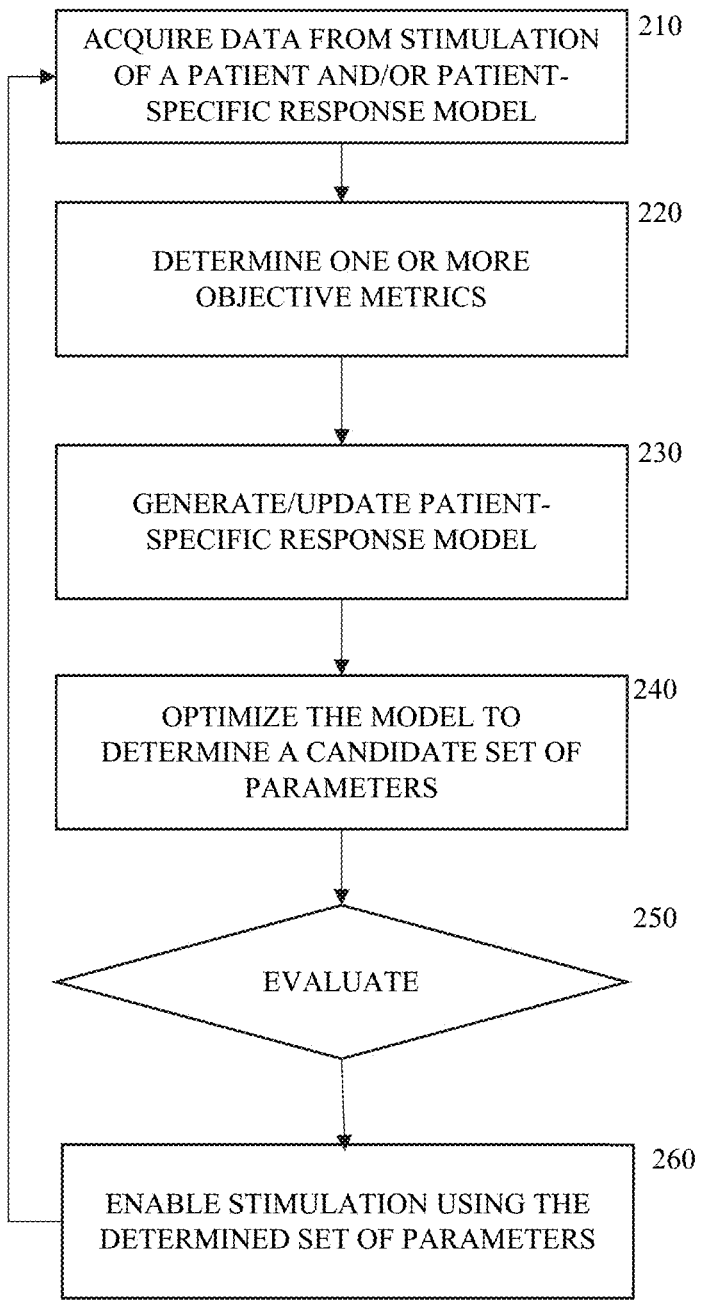
FIG. 2 is a flow chart illustrating an example of a method of determining an optimal set of stimulation parameters according to embodiments.

FIG. 2 shows flow chart 200 illustrating examples of a method of determining an optimal set of stimulation parameters according to certain embodiments. Operations described in flow charts 200 may be performed by a computing system, such as the device 110 described above with respect to FIG. 1 or a computing system described below with respect to FIG. 7. Although the flow charts 200 may describe the operations as a sequential process, in various embodiments, some of the operations may be performed in parallel or concurrently. In addition, the order of the operations may be rearranged. An operation may have additional steps not shown in the figure. In some embodiments, some operations may be optional. Embodiments of the method may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium.

Operations in flow charts 200 may begin at block 210, the device 110 may receive patient data collected during one or more testing sessions (or a period of time) and the set of stimulation parameters associated with the stimulation delivered by the system 120 to a patient during the testing session(s) and/or acquire the patient response model previously generated for that patient, from example, from the databases 150. For example, the patient data may be from a plurality of different testing sessions in which different tests (rest, postural, kinetic, etc.) were administered and the associated stimulation parameters may correspond to the parameters associated with the stimulation delivered by the system 120 during each test. The data for each testing session (or the period of time) may include the patient data acquired by one or more sensors and/or the clinician and the associated set of stimulation parameters.

In some embodiments, the device 110, at block 220, may determine the one or more objective metrics using the patient data for each testing session. The objective metrics may be a quantitative value representing (i) a rating or score of tremor severity and/or (ii) a rating or score of side effect severity described herein. In some embodiments, one or more objective metrics may be determined using the patient data for each testing session. In some embodiments, more than one objective metric related to tremor severity and/or side effect severity may be determined for a testing session.

In some embodiments, the device 110, at block 230, may generate a patient response model and/or update a patient response model previously generated for the patient using the objective metrics determined for each testing session and the associated set of stimulation parameters.

In some embodiments, the device 110 generate a patient response model based on a single objective metric that reflects the determined tremor and/or objective metrics associated with each setting tested. For example, the patient response model may be generated, for example, by applying an objective function to the metrics determined for each setting tested. For example, the single objective metric may be determined by applying the following objective function:

$$J_{DBS_i} = J_{SideEffect} + J_{tremor_i}$$

$$J_{tremor_i} = tremor_{DBS_i} - tremor_0$$

$$J_{SideEffect} = \begin{cases} 0 & \text{if no } SE \\ 1 & \text{if mild } SE \\ 4 & \text{if moderate } SE \\ 5 & \text{if severe } SE, \end{cases}$$

where $J_{tremor_i}$ is the tremor score improvement comparing to the baseline ($tremor_0$). $J_{tremor_i}$ could get any value in the [−4,4] interval depending on the baseline score (baseline is the score when the DBS is off) and the tremor score in the $DBS_i$ setting $J_{tremor_i}=0$ means no tremor improvement, $J_{tremor_i}<0$ show tremor score improvements, and $J_{tremor_i}>0$ show the cases where the score is worse than the baseline.

For example, in use, if there is a side effect report for the ith DBS setting, $J_{tremor_i}$ can be penalized by adding a positive value. If the side effect is mild, $J_{tremor_i}$ can be penalized by one. If the side effect is moderate, $J_{tremor_i}$ can be penalized by four because any tremor improvement with moderate SE can be considered as no improvement (ends up with a zero or positive $J_{DBS_i}$ score). If the SE is severe, $J_{tremor_i}$ can be penalized by more four, such as five, to avoid the optimizer to reach to that area again. This example represents how the objective for optimization is calculated in each step of optimization based on patient's response to different stimulation settings.

In some embodiments, at block 230, the patient response model may be generated using a multi-dimensional modeling approach, where each dimension reflects each objective metric. For example, the patient response model may be generated using parametric and nonparametric data-driven modeling techniques that adaptively model a patient's response to DBS settings. Parametric models may include linear models and generalized linear models.

By way of example, the patient response model may be generated using a nonparametric model, such as a Gaussian Process Regression (GPR) technique. In this example, the patient response models can be probabilistic models that represent the patient response. GPR can be characterized by its prior mean function and its positive-definite kernel, or covariance function. For example, $D_n=\{(x_i,y_i)\}$, i=1, . . . , n can denote the set of observations, where $x_i$ denotes the DBS parameters, e.g. stimulation amplitude, contact group, frequency, etc. and $y_i$ denotes the DBS-related objective metric. The GPR model can be defined by its mean m(x), and covariance function k, where the covariance function dictates the structure of the response functions that can be fit. The mean function can be used to estimate the patient response at each stimulation (parameter) setting and the covariance function can be used to represent the uncertainty of the estimated value.

In some embodiments, at block 230, the patient response model can be trained as a surrogate of the real objective function.

In some embodiments, at block 240, the device 110 may optimize the patient response model to determine a candidate set of stimulation parameters. For example, the device 110 may optimize the patient response model by optimizing a surrogate-dependent acquisition function, by using active learning algorithms, other machine learning algorithms, among others, or a combination thereof, to determine a candidate set of stimulation parameters.

This way, the device 110 may use the patient response model as a map to identify important regions in the DBS parameter space. For example, the patient response model can determine a mapping between the stimulation parameters and the objective metrics. The important regions in the parameter space can be determined based on the objective measure. For example, if the objective metric quantifies tremor severity, the areas in the parameter space that minimize tremor severity (as measured by the objective measures) may represent an region in the DBS parameter space to explore.

In some embodiments, at block 250, the device 110 may evaluate whether the candidate set of stimulation parameters determined at block 240 meets the optimal criteria to determine whether it qualifies as an optimal set of stimulation parameters. By way of example, if the optimization algorithm determines that there was a convergence to a solution (e.g., minimizes or maximizes the an objective function) and/or a stopping criteria such as a maximum number of iterations has been reached, the candidate set of stimulation parameters may be considered to be the optimal set of stimulation parameters.

In some embodiments, the device 110 may be configured to automatically optimize the stimulation parameters until optimal criteria is met. For example, if the device 110 determines that the candidate set of stimulation parameters does not meet optimal criteria, then the device 110 may enable the device 110 to electrically stimulate the patient using the candidate set of simulation parameters at block 260 and the device 110 may continue to repeat the method illustrated by the flow chart 200, until the device 110 determines that the candidate set of stimulation parameters is the optimal set of stimulation parameters for the patient at block 250.

If the device 110 determines that the candidate set of stimulation parameters meets optimal criteria, then the device 110 may enable the system 120 to electrically stimulate the patient using the optimal set of simulation parameters at block 260. The device 110 may end the iterative process until the next testing session or data collection period.

In some embodiments, the device 110 may engage the clinician in the optimization of the stimulation parameters. For example, the device 110 may output the candidate set of stimulation parameters or the optimal set of stimulation parameters determined at block 240 with and/or without the patient response model generated at block 230. The device 110 may await to receive instructions before enabling stimulation using the determined set of parameters.

EXAMPLES

As described above, techniques (referred to in this example a "Change Point Decoder" (CPD)) disclosed herein can be used to determine a set of optimal DBS parameters using a patient response (surrogate model) generated from patient data collected during tests performed during performance session(s). A study has been conducted using techniques disclosed herein to determine optimal DBS parameters.

I. Methods

A. Experimental Setup and Data Collections

In this study, data that was previously collected during the monopolar screening in a recent study. A. Haddock, K. T. Mitchell, A. Miller, J. L. Ostrem, H. J. Chizeck, and S. Miocinovic, "Automated Deep Brain Stimulation Programming for Tremor," *IEEE Trans. Neural Syst. Rehabil. Eng.*, vol. 26, no. 8, pp. 1618-1625, August 2018. Patients who had ET or tremor-dominant PD and were implanted with Medtronic Activa PC series neurostimulator systems for at least six months and who were thought to have arrived at optimal DBS settings through clinical programming. Data was collected during an automated DBS programming experiment using a custom software application developed for a Windows PC laptop. A pseudorandom monopolar screen for which the evaluation of tremor and side effect severity was performed and command over DBS parameters was under automated control by the computer program. Typically 24 total settings was tested by changing the stimulation amplitude from 0-5V and for four different stimulation contacts.

B. Framework

Figure 3:
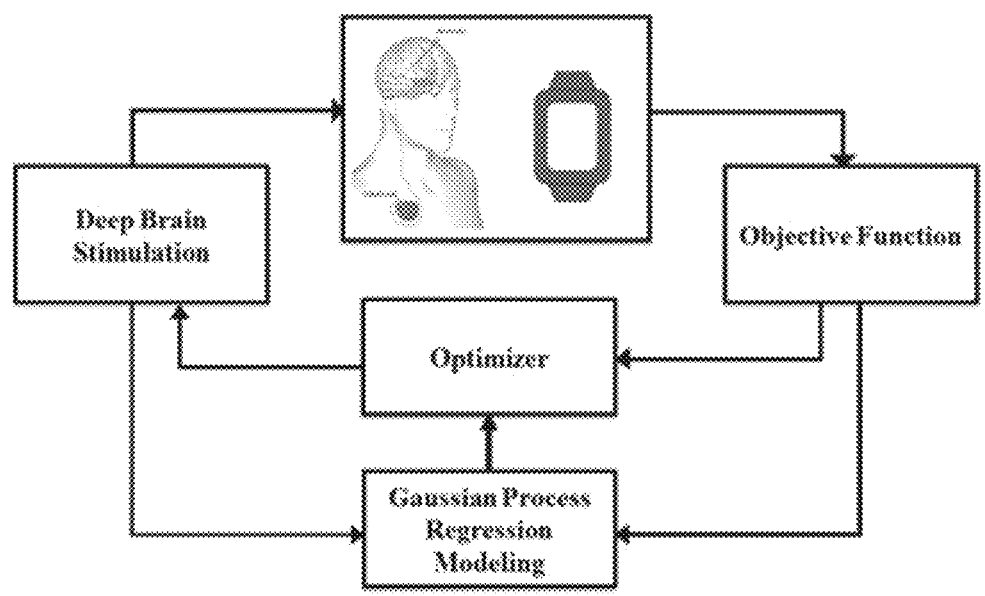
FIG. 3 shows an example a framework used in a study of the method according to embodiments.

FIG. 3 illustrates a high-level overview of the framework used in the study. The framework is a real-time patient-specific framework for automated optimization of deep brain stimulation parameters. method addresses the most concerning issue regarding the current clinical approaches using advanced deep brain stimulation systems because the method selects the best stimulation parameters effectively with the minimum possible set of tests on patients. Bayesian optimization was used as the optimization algorithm for two main reasons. First, it is a sample efficient algorithm and appropriate for cases where the objective function is unknown and expensive to evaluate. Second, it takes the uncertainty of the model into account using the surrogate model. Here a Gaussian Process Regression (GPR) model is selected as the surrogate model.

Before testing the performance of the framework on patients its potential benefits were explored through an offline and simulation-based analysis. The offline analysis using the collected data was designed at the previous study [Ibid] to explore the performance of Bayesian optimization in finding the optimal stimulation settings. Since there was no access to patients directly, the effect of stimulation parameters, i.e. stimulation amplitude and stimulation contact, on tremor ratings was modeled using a GPR model and utilized this model as a surrogate to the real objective function. To have a fully automated framework, instead of modeling the effect of stimulation parameters on the neurologist provided tremor evaluation, the model was built based on predicted clinical scores. Clinical scores were predicted by a multinomial logistic regression (MLR) model using the accelerometer and gyroscope data based on the neurologist tremor evaluation as discussed with more details in [Ibid].

C. Gaussian Process Regression Model

The effect of stimulation parameters on the clinical outcomes using Gaussian Process (GP) regression models was used as a surrogate of the real objective function. A patient-specific GP regression model can provide the possibility of utilizing and evaluating the model-based closed-loop optimization algorithms to identify the best stimulation parameters for each patient.

A Gaussian process can be considered as a distribution over functions. It is a collection of random variables, any finite number of which have a joint Gaussian distribution. In this study, our training dataset includes stimulation parameters, i.e., stimulation amplitude and stimulation contact, and their corresponding predicted clinical scores. The training dataset containing n observations can be denoted as $D=\{(x_i, y_i)|i=1, \ldots, n\}$, where $x_i$ shows the vector of stimulation parameters of size 1×2 and $y_i = +\varepsilon$ is a scalar valued noisy observation of clinical score for $x_i$ and $\varepsilon$ is the additive white gaussian noise. A UP is a nonparametric model that is fully characterized by its mean and covariance function as following $$f(x) \sim GP(m(x), K(x,x')), \quad (1)$$

where the mean function can be defined $m(x)=E[f(x)]$ and the covariance function as $K(x,x')=E[(f(x)-m(x))(f(x')-m(x'))]$. For the sake of simplicity, the mean can be considered as $m(x)=0$ without loss of generality. The knowledge from the training dataset, i.e. prior distribution in (1) can be incorporated to make predictions at any new test point $(x_*, f_*)$, where $f_*=f(x_*)$. The predictive conditional distribution of f* given the training data and test input can be calculated as in $$f_*|X,y,X_* \sim N(\bar{f}_*, \text{cov}(f_*)), \quad (2)$$

where, ff$_*$=E[f$_*$|X,y,X$_*$]=K(X$_*$,X)[K(X,X)+$\sigma_n^2$I]$^{-1}$y, cov(f$_*$)=K(X$_*$,X$_*$)−K(X$_*$,X)[K(X,X)+$\sigma_n^2$I]$^{-1}$K(X,X$_*$), and $\sigma_n^2$ denotes the variance of $\varepsilon$.

In this study, the Matern kernel function was utilized due to its simplicity and common use as in $$K_{MATERN3}(x,x')=\sigma_f^2 \exp(-\sqrt{3}r(1+\sqrt{3}r))+\sigma_n^2 I \quad (3)$$

where $r^2=(x-x')^T\Lambda(x-x')$ and $\Lambda$ is a diagonal matrix of squared length scales. $\sigma_f^2$, the length-scales, and the noise variance $\sigma_n^2$ are hyperparameters of our covariance function. These hyperparameters are then optimized by optimizing the marginal likelihood p(y|X) with respect to the hyperparameters.

D. Objective Function

The objective function is the evaluated clinical response, i.e., clinical tremor assessment score, over the stimulation parameters space which is expensive to evaluate. After evaluating the clinical scores, the data and estimated the patient-specific objective functions was used using GPR model. GP regression models was employed because they are data efficient, flexible and able to handle uncertainty about the objective functions. This model can be used for an offline, and simulation-based evaluation of the performance of Bayesian optimization algorithm in parameter selection for each patient which is an important step towards the real-time implementation.

E. Bayesian Optimization

Bayesian optimization is a popular global optimization problem in which the objective function is unknown or expensive to evaluate. The objective function that was used, as defined in the previous section, does not have a close form. However, the objective function can be evaluated by sampling from the patient-specific GPR models. Bayesian optimization is a sequential model-based optimization algorithm that tries to sequentially find the optimum in two steps. First, it builds a surrogate model instead of the latent objective function based on the available data at each iteration. A common surrogate model is the GPR prior. In this study, the GPR model with Matern kernel was considered. Second, it proposes the next stimulation setting to evaluate the objective function by optimizing a surrogate-dependent acquisition function. The popular Upper Confidence Bound (UCB) acquisition function that has the following form can be deployed $$\alpha_{GP-UCB}(x;D_n)=\mu(x)+\sqrt{\beta_t}\sigma(x), \quad (4)$$

where $\beta_t$ are proper constants. See N. Srinivas, A. Krause, S. M. Kakade, and M. Seeger, "Gaussian Process Optimization in the Bandit Setting: No Regret and Experimental Design," December 2009.

During the burn-in phase of Bayesian optimization, the objective function is evaluated at five random stimulation settings. Then, a GPR prior based on these initial evaluations of the burn-in phase is employed. Thereafter, a new stimulation setting is sequentially selected by optimizing the UCB acquisition function to be evaluated at next iteration. At each iteration, the dataset is augmented and the surrogate GPR prior is updated. It is of great importance to define a budget to stop exploring the objective function once the budget is exhausted and/or to come up with a stopping criterion. Here, since a simulation-base study was conducted, defining the stopping criteria is not necessary.

II. Results

The effect of stimulation parameters on patient's clinical response was modeled using GPR model. This model was used to investigate the problem of automated DBS optimization.

A. Automated Prediction of Clinical Tremor Ratings

Figure 4A:
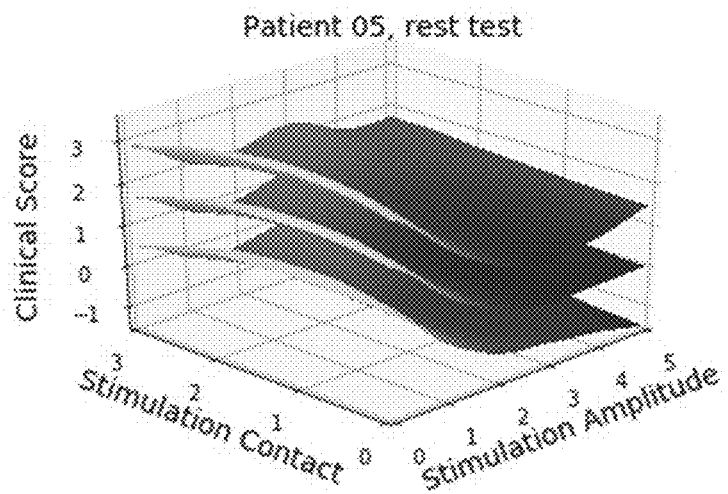
FIGS. 4A and 4B show a patient-specific GP regression model for rest tremor test.
Figure 4B:
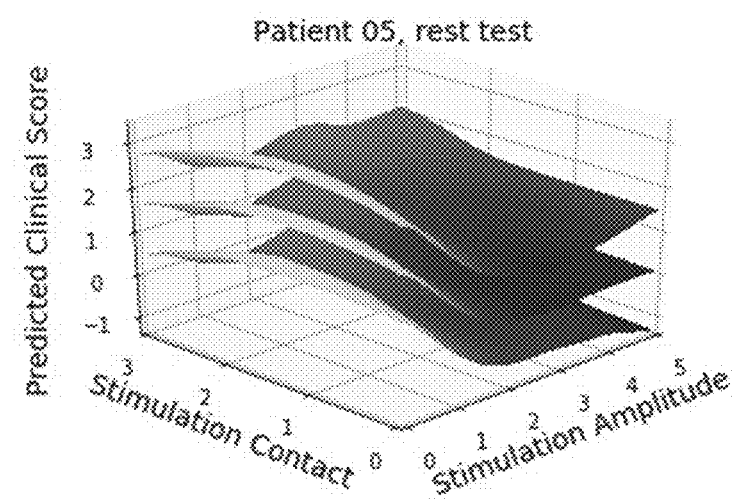

As mentioned earlier, in order to have a fully automated framework, the GPR models was built based on the predicted clinical scores using a MLR model. The GPR models based on the predicted clinical scores must be consistent with the models based on the neurologists provided tremor ratings in terms of the optimal stimulation setting. In other words, using the predicted clinical scores instead of the neurologists provided tremor ratings should not considerably affect the location of optimum stimulation setting in GPR models. FIGS. 4A and 4B compare the results of modeling the effect of stimulation parameters on the neurologists provided tremor ratings and the predicted tremor ratings. This figure illustrates the consistency of GPR models using the predicted tremor ratings.

FIGS. 4A and 4B show the patient-specific GP regression model for rest tremor test. FIG. 4A demonstrates the modeled effect of stimulation settings on the clinical scores evaluated by neurologists. FIG. 4B shows the same model on predicted clinical scores modeled by a multinomial logistic regression method for the same patient. The intermediate surfaces show the mean of the GP regression model and the upper and lower surfaces reflect the uncertainty of the model around the mean.

B. Test and Patient Variations

Figure 5A:
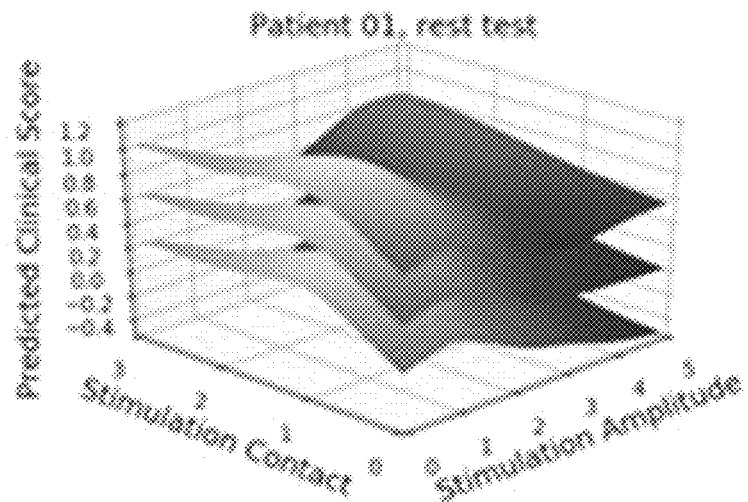
FIGS. 5A-C demonstrate the results of GPR modeling for one patient among different tests.
Figure 5B:
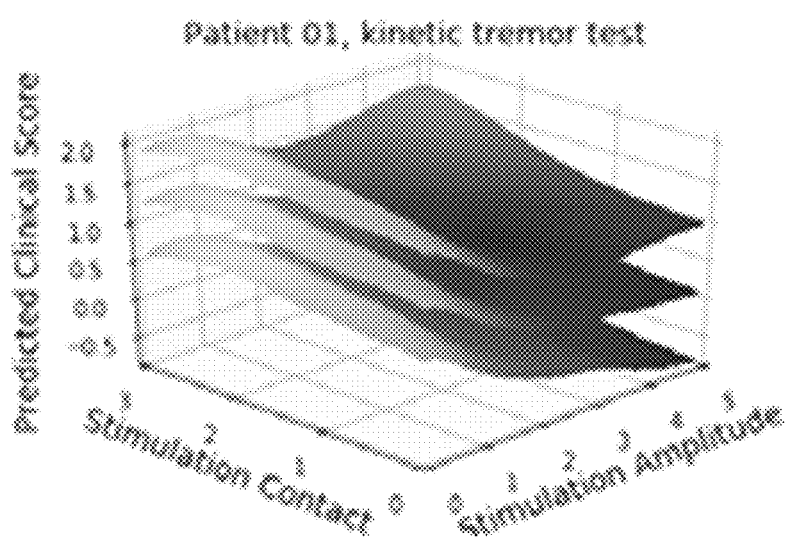
Figure 5C:
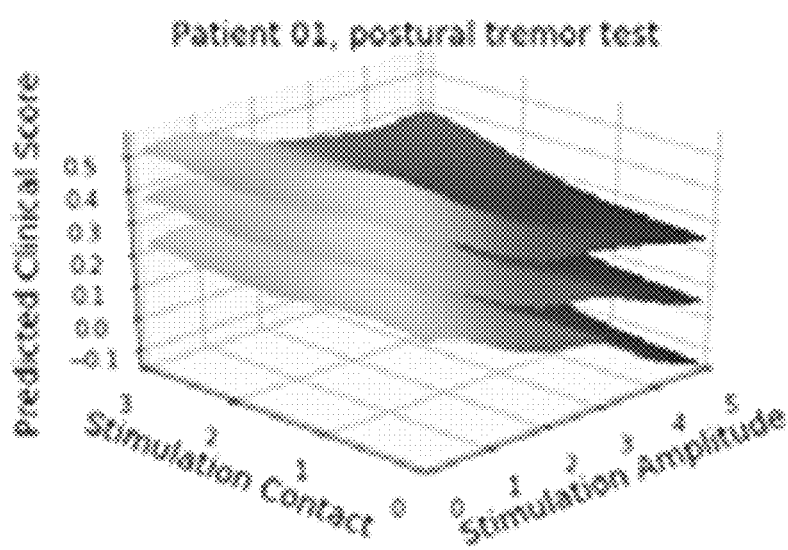

An advantage of modeling the effect of stimulation parameters on tremor rating scores is that the variability of different patient responses in various clinical tests such as rest, kinetic, postural tremor, and wrist turning tests, can be investigated. FIGS. 5A-C demonstrate the results of GPR modeling for one patient among different tests. FIG. 5A shows the results of GPR modeling for one patient for a rest test, FIG. 5B shows the results of GPR modeling for one patient for a kinetic tremor test, and FIG. 5C shows the results of GPR modeling for one patient for a postural tremor test. As it is shown in FIGS. 5A-C, the best stimulation parameter which minimizes the clinical scores, shown in dark gray, is not precisely consistent among different clinical tests for each patient. Besides, by comparing the models in FIGS. 4A-B and FIGS. 5A-C, different patients' responses to stimulation parameters varies even during a unique clinical test. Therefore, modeling the effect of stimulation settings should be patient-specific.

C. Bayesian Optimization Analysis

Figure 6A:
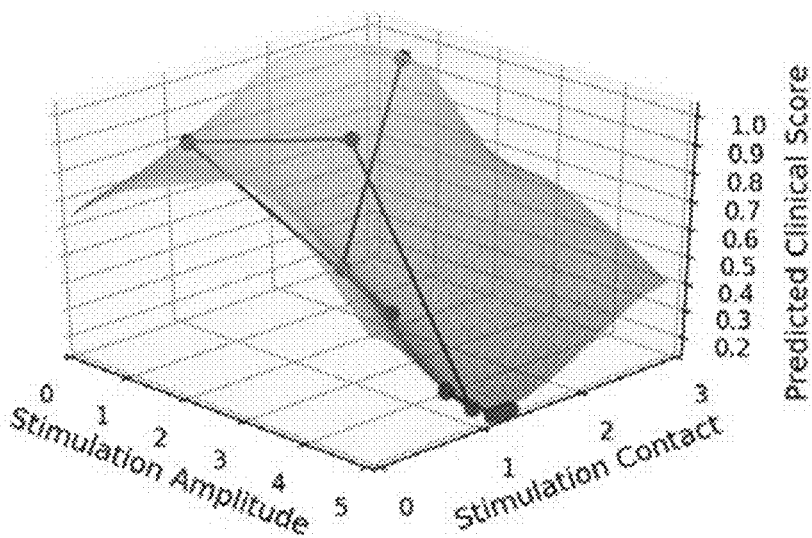
FIGS. 6A and B show the performance of the Bayesian optimizer for one patient during the rest test.
Figure 6B:
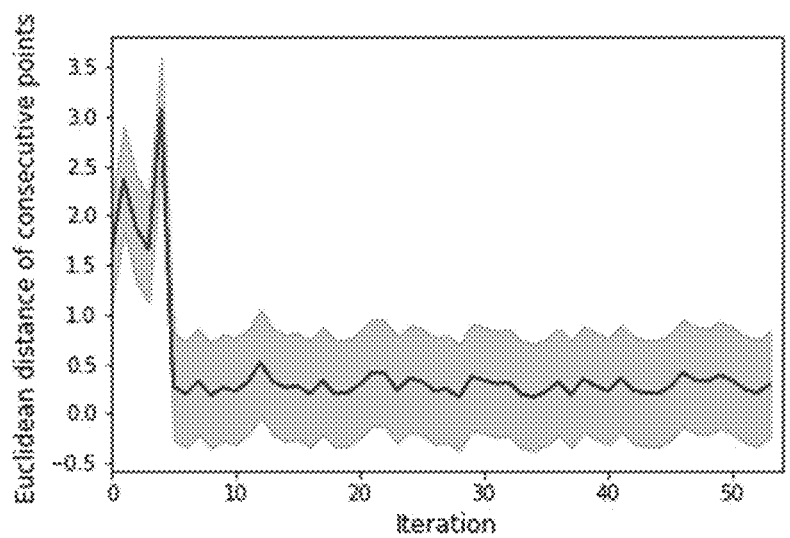
FIG. 6B shows the mean and confidence interval of Euclidean distance of consecutive points selected by the acquisition function for 55 iterations.

The performance of Bayesian optimization algorithm was assessed in finding the optimum stimulation parameters. The GPflowOpt library was employed for Bayesian optimization implementation. First, during the burn-in phase the objective function is evaluated at five random stimulation settings. Performance of the Bayesian optimizer is evaluated for five trials. FIGS. 6A and B show the performance of the Bayesian optimizer for one patient during the rest test. FIG. 6A illustrates the trajectory of points that was selected by the acquisition function to be evaluated at each iteration during one trial of running the optimizer. The fact that the optimizer rapidly converges to the area close to the optimum point is an interesting characteristic of Bayesian optimizer which makes it sample-efficient. FIG. 6B shows the mean and confidence interval of Euclidean distance of consecutive points selected by the acquisition function for 55 iterations. The simulations and analysis indicate that Bayesian optimizer is a promising approach that can find the optimum with significantly lower number of evaluations.

III. Discussion

The current work demonstrates the feasibility of the proposed framework for DBS parameter selection rapidly and effectively for each patient in a real-time and closed-loop manner. This framework facilitates the procedure of optimal parameter selection especially for geographic locations where patients does not have access to clinics. This framework provides the possibility of not only removing the clinician from the loop, but also performing the parameter selection process considerably faster relative to brute-force search methods. In other words, the search can be ended as soon as the result of tremor evaluation was adequate based on a predefined threshold instead of completing the entire predefined set of parameters of brute-force search algorithm. Moreover, the optimizer allows for a finer resolution assessment of tremor severity over the parameter space.

IV. Conclusion

In this study, a framework for designing and testing optimization algorithms was developed for automated optimization of deep brain stimulation parameters. Prolonged programming sessions could exhaust the patients which affects the quality and accuracy of tremor evaluation tests. Therefore, it is of great importance to come up with an effective approach to search for the optimal stimulation setting with the minimal tremor evaluation trials.

Figure 7:
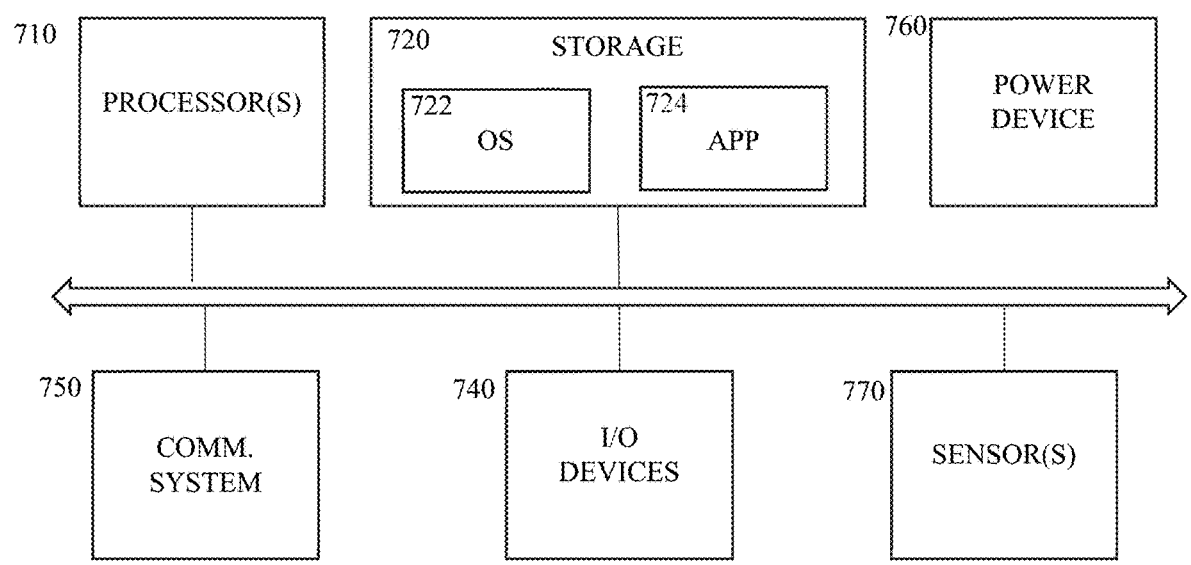
FIG. 7 is a simplified block diagram of an example of a computing system for implementing certain embodiments disclosed herein.

FIG. 7 depicts a block diagram of an example computing system 700 for implementing certain embodiments. For example, in some aspects, the computer system 700 may include computing systems associated with a device (e.g., the device 110) performing one or more processes (e.g., FIG. 2) disclosed herein. The block diagram illustrates some electronic components or subsystems of the computing system. The computing system 700 depicted in FIG. 7 is merely an example and is not intended to unduly limit the scope of inventive embodiments recited in the claims. One of ordinary skill in the art would recognize many possible variations, alternatives, and modifications. For example, in some implementations, the computing system 700 may have more or fewer subsystems than those shown in FIG. 7, may combine two or more subsystems, or may have a different configuration or arrangement of sub systems.

In the example shown in FIG. 7, the computing system 700 may include one or more processing units 710 and storage 720. The processing units 710 may be configured to execute instructions for performing various operations, and can include, for example, a micro-controller, a general-purpose processor, or a microprocessor suitable for implementation within a portable electronic device, such as a Raspberry Pi. The processing units 710 may be communicatively coupled with a plurality of components within the computing system 700. For example, the processing units 710 may communicate with other components across a bus. The bus may be any subsystem adapted to transfer data within the computing system 700. The bus may include a plurality of computer buses and additional circuitry to transfer data.

In some embodiments, the processing units 710 may be coupled to the storage 720. In some embodiments, the storage 720 may offer both short-term and long-term storage and may be divided into several units. The storage 720 may be volatile, such as static random access memory (SRAM) and/or dynamic random access memory (DRAM), and/or non-volatile, such as read-only memory (ROM), flash memory, and the like. Furthermore, the storage 720 may include removable storage devices, such as secure digital (SD) cards. The storage 720 may provide storage of computer readable instructions, data structures, program modules, audio recordings, image files, video recordings, and other data for the computing system 700. In some embodiments, the storage 720 may be distributed into different hardware modules. A set of instructions and/or code might be stored on the storage 720. The instructions might take the form of executable code that may be executable by the computing system 700, and/or might take the form of source and/or installable code, which, upon compilation and/or installation on the computing system 700 (e.g., using any of a variety of generally available compilers, installation programs, compression/decompression utilities, and the like), may take the form of executable code.

In some embodiments, the storage 720 may store a plurality of application modules 724, which may include any number of applications, such as applications for controlling input/output (I/O) devices 740 (e.g., a sensor (e.g., sensor(s) 770, other sensor(s), etc.)), a switch, a camera, a microphone or audio recorder, a speaker, a media player, a display device, etc.). The application modules 724 may include particular instructions to be executed by the processing units 710. In some embodiments, certain applications or parts of the application modules 724 may be executable by other hardware modules, such as a communication subsystem 750. In certain embodiments, the storage 720 may additionally include secure memory, which may include additional security controls to prevent copying or other unauthorized access to secure information.

In some embodiments, the storage 720 may include an operating system 722 loaded therein, such as an Android operating system or any other operating system suitable for mobile devices or portable devices. The operating system 722 may be operable to initiate the execution of the instructions provided by the application modules 724 and/or manage other hardware modules as well as interfaces with a communication subsystem 750 which may include one or more wireless or wired transceivers. The operating system 722 may be adapted to perform other operations across the components of the computing system 700 including threading, resource management, data storage control, and other similar functionality.

The communication subsystem 750 may include, for example, an infrared communication device, a wireless communication device and/or chipset (such as a Bluetooth® device, an IEEE 802.11 (Wi-Fi) device, a WiMax device, cellular communication facilities, and the like), NFC, Zig-Bee, and/or similar communication interfaces. The computing system 700 may include one or more antennas (not shown in FIG. 7) for wireless communication as part of the communication subsystem 750 or as a separate component coupled to any portion of the system.

Depending on desired functionality, the communication subsystem 750 may include separate transceivers to communicate with base transceiver stations and other wireless devices and access points, which may include communicating with different data networks and/or network types, such as wireless wide-area networks (WWANs), WLANs, or wireless personal area networks (WPANs). A WWAN may be, for example, a WiMax (IEEE 802.9) network. A WLAN may be, for example, an IEEE 802.11x network. A WPAN may be, for example, a Bluetooth network, an IEEE 802.15x, or some other types of network. The techniques described herein may also be used for any combination of WWAN, WLAN, and/or WPAN. In some embodiments, the communications subsystem 750 may include wired communication devices, such as Universal Serial Bus (USB) devices, Universal Asynchronous Receiver/Transmitter (UART) devices, Ethernet devices, and the like. The communications subsystem 750 may permit data to be exchanged with a network, other computing systems, and/or any other devices described herein. The communication subsystem 750 may include a means for transmitting or receiving data, such as identifiers of portable goal tracking devices, position data, a geographic map, a heat map, photos, or videos, using antennas and wireless links. The communication subsystem 750, the processing units 710, and the storage 720 may together comprise at least a part of one or more of a means for performing some functions disclosed herein.

The computing system 700 may include one or more I/O devices 740, such as sensors 770, a switch, a camera, a microphone or audio recorder, a communication port, or the like. For example, the I/O devices 740 may include one or more touch sensors or button sensors associated with the buttons. The touch sensors or button sensors may include, for example, a mechanical switch or a capacitive sensor that can sense the touching or pressing of a button.

In some embodiments, the I/O devices 740 may include a microphone or audio recorder that may be used to record an audio message. The microphone and audio recorder may include, for example, a condenser or capacitive microphone using silicon diaphragms, a piezoelectric acoustic sensor, or an electret microphone. In some embodiments, the microphone and audio recorder may be a voice-activated device. In some embodiments, the microphone and audio recorder may record an audio clip in a digital format, such as MP3, WAV, WMA, DSS, etc. The recorded audio files may be saved to the storage 720 or may be sent to the one or more network servers through the communication subsystem 750.

In some embodiments, the I/O devices 740 may include a location tracking device, such as a global positioning system (GPS) receiver. In some embodiments, the I/O devices 740 may include a wired communication port, such as a micro-USB, Lightning, or Thunderbolt transceiver.

The I/O devices 740 may also include, for example, a speaker, a media player, a display device, a communication port, or the like. For example, the I/O devices 740 may include a display device, such as an LED or LCD display and the corresponding driver circuit. The I/O devices 740 may include a text, audio, or video player that may display a text message, play an audio clip, or display a video clip.

The computing system 700 may include a power device 760, such as a rechargeable battery for providing electrical power to other circuits on the computing system 700. The rechargeable battery may include, for example, one or more alkaline batteries, lead-acid batteries, lithium-ion batteries, zinc-carbon batteries, and NiCd or NiMH batteries. The computing system 700 may also include a battery charger for charging the rechargeable battery. In some embodiments, the battery charger may include a wireless charging antenna that may support, for example, one of Qi, Power Matters Association (PMA), or Association for Wireless Power (A4WP) standard, and may operate at different frequencies. In some embodiments, the battery charger may include a hard-wired connector, such as, for example, a micro-USB or Lightning® connector, for charging the rechargeable battery using a hard-wired connection. The power device 760 may also include some power management integrated circuits, power regulators, power convertors, and the like.

In some embodiments, the computing system 700 may include one or more sensors 770. The sensors 770 may include, for example, the sensors as described above.

The computing system 700 may be implemented in many different ways. In some embodiments, the different components of the computing system 700 described above may be integrated to a same printed circuit board. In some embodiments, the different components of the computing system 700 described above may be placed in different physical locations and interconnected by, for example, electrical wires. The computing system 700 may be implemented in various physical forms and may have various external appearances. The components of computing system 700 may be positioned based on the specific physical form.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

The foregoing method descriptions and the process flow diagrams are provided merely as illustrative examples and are not intended to require or imply that the operations of various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

While the terms "first" and "second" are used herein to describe data transmission associated with a subscription and data receiving associated with a different subscription, such identifiers are merely for convenience and are not meant to limit various embodiments to a particular order, sequence, type of network or carrier.

Various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such embodiment decisions should not be interpreted as causing a departure from the scope of the claims.

The hardware used to implement various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing systems, (e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more example embodiments, the functions described may be implemented in hardware, software, firmware, or any combination thereof. If implemented in software, the functions may be stored as one or more instructions or code on a non-transitory computer readable medium or non-transitory processor-readable medium. The operations of a method or algorithm disclosed herein may be embodied in a processor-executable software module, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AC, BC, AA, ABC, AAB, AABBCCC, and the like.

Further, while certain embodiments have been described using a particular combination of hardware and software, it should be recognized that other combinations of hardware and software are also possible. Certain embodiments may be implemented only in hardware, or only in software, or using combinations thereof. In one example, software may be implemented with a computer program product containing computer program code or instructions executable by one or more processors for performing any or all of the steps, operations, or processes described in this disclosure, where the computer program may be stored on a non-transitory computer readable medium. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques, including, but not limited to, conventional techniques for inter-process communications, and different pairs of processes may use different techniques, or the same pair of processes may use different techniques at different times.

The disclosures of each and every publication cited herein are hereby incorporated herein by reference in their entirety.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for determining a set of stimulation parameters for a neurostimulation device, comprising:
   receiving, at a computerized system, (i) patient data and (ii) at least one set of stimulation parameters associated with stimulation delivered by a neurostimulation device to a patient for a period of time;
   determining one or more objective metrics using the patient data for each set of stimulation parameters for the period of time, the one or more objective metrics being a quantitative value that represents (i) a rating or score of tremor severity and/or (ii) a rating or score of side effect severity associated with the set of stimulation parameters;
   generating a response model specific to the patient using the one or more objective metrics and the associated set of stimulation parameters; and
   applying an optimization algorithm to the generated response model to determine a candidate set of one or more stimulation parameters.

2. The method according to claim 1, further comprising:
   enabling the neurostimulation device to electrically stimulate a brain of the patient using the candidate set of one or more stimulation parameters for the period of time;
   determining one or more objective metrics using the patient data for candidate set of stimulation parameters; and
   updating the response model specific to the patient using the one or more objective metrics and the associated candidate set of stimulation parameters.

3. The method according to claim 1, further comprising:
evaluating the candidate set of stimulation parameters to determine whether the candidate set of stimulation parameters meets criteria; and
enabling the neurostimulation device to electrically stimulate a brain of the patient using the candidate set of stimulation parameters that meet the criteria.

4. The method according to claim 1, further comprising:
enabling the neurostimulation device to electrically stimulate a brain of the patient using the candidate set of one or more stimulation parameters.

5. The method according to claim 1, wherein the optimization algorithm is a Bayesian optimization algorithm.

6. The method according to claim 1, wherein:
the one or more objective metrics includes a plurality of objective metrics for the set of stimulation parameters; and
the response model is generated based on a single objective metric that is a combination of the plurality of objective metrics.

7. The method according to claim 1, wherein the response model is a multi-objective patient response model.

8. The method according to claim 7, wherein the response model is a probabilistic model of the one or more objective metrics.

9. The method according to claim 1, wherein the stimulation parameters include electrode configuration, amplitude, pulse width, pulse rate, duration, among others, or a combination thereof.

10. The method according to claim 1, wherein the patient data and the set of stimulation parameters associated stimulation delivered to a patient was collected during one or more testing sessions.

11. A system, comprising:
one or more processors; and
one or more hardware storage devices having stored thereon computer-executable instructions which are executable by the one or more processors to cause a computing system to perform at least the following:
receiving (i) patient data and (ii) at least one set of stimulation parameters associated with stimulation delivered to a patient by a neurostimulation device for a period of time;
determining one or more objective metrics using the patient data for each set of stimulation parameters for the period of time, the one or more objective metrics being a quantitative value that represents (i) a rating or score of tremor severity and/or (ii) a rating or score of side effect severity associated with the set of stimulation parameters;
generating a response model specific to the patient using the one or more objective metrics and the associated set of stimulation parameters; and
applying an optimization algorithm to the generated response model to determine a candidate set of one or more stimulation parameters.

12. The system according to claim 11, wherein the one or more processors are further configured to cause the computing system to perform at least the following:
enabling the neurostimulation device to electrically stimulate a brain of the patient using the candidate set of one or more stimulation parameters for the period of time;
determining one or more objective metrics using the patient data for candidate set of stimulation parameters; and
updating the response model specific to the patient using the one or more objective metrics and the associated candidate set of stimulation parameters.

13. The system according to claim 11, wherein the one or more processors are further configured to cause the computing system to perform at least the following:
evaluating the candidate set of stimulation parameters to determine whether the candidate set of stimulation parameters meets criteria; and
enabling the neurostimulation device to electrically stimulate a brain of a patient using the candidate set of stimulation parameters that meet the criteria.

14. The system according to claim 11, wherein the one or more processors are further configured to cause the computing system to perform at least the following:
enabling the neurostimulation device to electrically stimulate a brain of the patient using the candidate set of one or more stimulation parameters.

15. The system according to claim 11, wherein the optimization algorithm is a Bayesian optimization algorithm.

16. The system according to claim 11, wherein:
the one or more objective metrics includes a plurality of objective metrics for the set of stimulation parameters; and
the response model is generated based on a single objective metric that is a combination of the plurality of objective metrics.

17. The system according to claim 11, wherein the response model is a multi-objective patient response model.

18. The system according to claim 17, wherein the response model is a probabilistic model of the one or more objective metrics.

19. The system according to claim 11, wherein the stimulation parameters include electrode configuration, amplitude, pulse width, pulse rate, duration, among others, or a combination thereof.

20. The system according to claim 11, wherein the patient data and the set of stimulation parameters associated stimulation delivered to a patient was collected during one or more testing sessions.

* * * * *